(12) United States Patent
Hacker et al.

(10) Patent No.: US 8,801,184 B2
(45) Date of Patent: Aug. 12, 2014

(54) SYSTEM FOR THE IMPROVED IMAGING OF EYE STRUCTURES

(75) Inventors: Martin Hacker, Jena (DE); Rudolf Murai von Bünau, Jena (DE); Burkhard Wagner, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 26 days.

(21) Appl. No.: 13/696,030

(22) PCT Filed: Apr. 23, 2011

(86) PCT No.: PCT/EP2011/002073
§ 371 (c)(1),
(2), (4) Date: Jan. 15, 2013

(87) PCT Pub. No.: WO2011/137985
PCT Pub. Date: Nov. 10, 2011

(65) Prior Publication Data
US 2013/0107209 A1 May 2, 2013

(30) Foreign Application Priority Data
May 3, 2010 (DE) .......................... 10 2010 019 657

(51) Int. Cl.
*A61B 3/14* (2006.01)
*A61B 3/00* (2006.01)

(52) U.S. Cl.
USPC .......................................... 351/206; 351/246

(58) Field of Classification Search
USPC ................................................. 351/200–246
See application file for complete search history.

(56) References Cited

U.S. PATENT DOCUMENTS

| 5,321,501 A | 6/1994 | Swanson et al. |
| 6,654,127 B2 | 11/2003 | Everett et al. |

(Continued)

FOREIGN PATENT DOCUMENTS

| DE | 196 24 167 A1 | 1/1997 |
| DE | 10 2009 041 996 A1 | 3/2011 |
| EP | 1 337 803 A1 | 8/2003 |
| EP | 1 925 253 A1 | 5/2008 |

OTHER PUBLICATIONS

Wolfgang Drexler, James G. Fujimoto, "Optical Coherence Tomography" (with 758 figures), Library of Congress Control No. 2007943142, ISSN 16-18-7210, ISBN 978-3-540, Springer-Verlag Berlin Heidelberg Jan. 2008.

(Continued)

*Primary Examiner* — Mohammed Hasan
(74) *Attorney, Agent, or Firm* — Patterson Thuente Pedersen, P.A.

(57) ABSTRACT

A system for the improved imaging of eye structures based on optical coherence tomography. The system includes an interferometric measuring arrangement, which has an optical element arranged in the measurement arm or reference arm for influencing the polarization state of the light before the light is interferometrically superimposed, a scanning unit arranged in the measurement arm for implementing OCT scans, a detector for recording the produced interference pattern, and an evaluating and documenting unit. At least two different polarization states of the light are produced. The interference patterns produced in the interferometric measuring arrangement are recorded and forwarded to the evaluating and documenting unit which reconstructs OCT scans from the transmitted interference patterns, combines the OCT scans, and presents and/or stores the resulting OCT signals. The system can be used for pachymetry in addition to the pre- and post-operative imaging for analysis and measurement.

16 Claims, 3 Drawing Sheets

(56) References Cited

U.S. PATENT DOCUMENTS

| | | |
|---|---|---|
| 6,769,769 B2 | 8/2004 | Podoleanu et al. |
| 6,927,860 B2 | 8/2005 | Podoleanu et al. |
| 7,145,661 B2 | 12/2006 | Hitzenberger |
| 7,187,450 B2 | 3/2007 | Drabarek |
| 7,330,270 B2 | 2/2008 | O'Hara et al. |
| 7,359,062 B2 | 4/2008 | Chen et al. |
| 7,365,856 B2 | 4/2008 | Everett et al. |
| 7,400,410 B2 | 7/2008 | Baker et al. |
| 2002/0196446 A1* | 12/2002 | Roth et al. .................. 356/479 |
| 2005/0018137 A1 | 1/2005 | Barth et al. |
| 2005/0171438 A1 | 8/2005 | Chen et al. |
| 2007/0038040 A1 | 2/2007 | Cense et al. |
| 2007/0291277 A1 | 12/2007 | Everett et al. |
| 2009/0247862 A1* | 10/2009 | Meyer et al. ................ 600/425 |
| 2010/0014051 A1* | 1/2010 | Rathjen ....................... 351/206 |
| 2012/0188509 A1* | 7/2012 | Hogan ......................... 351/206 |

OTHER PUBLICATIONS

Adrian H. Bachmann et al: "Resonant Doppler flow imaging and optical vivisection of retinal blood vessels". Optics Express, vol. 15, No. 2. Jan. 22, 2007, p. 408, XP55005260, ISSN: 1094-4087, DOI: 10.1364/OE.15.000408 cited in the application the whole document.

B. Cense et al.: Thickness and Birefringence of Healthy Retinal Nerve Fiber Layer Tissue Measured with Polarization-Sensitive Optical Coherence Tomography.. 45. 2004. 2606-2612. Inverstigative Ophthalmology & Visual Science [online], Aug. 2004.

E. Götzinger et al.: High speed spectra domain polarizatin sensitive optical coherence tomography of the human retina. 13, 2005, 25, 10217-10229. Optics Express [online], Dec. 12, 2005.

Yoshiaki Yasuno et al., "Investigation of post-glaucoma-surgery structures by three-dimensional and polarization sensitive anterior eye segment optical coherence tomography", Optics Express 3996, Mar. 2, 2009/vol. 17, No. 5, 17 pages.

* cited by examiner

SYSTEM FOR THE IMPROVED IMAGING OF EYE STRUCTURES

PRIORITY CLAIM

The present application is a National Phase entry of PCT Application No. PCT/EP2011/002073, filed Apr. 23, 2011, which claims priority from German Application No 10 2010 019 657.6, filed May 3, 2010, the disclosures of which are hereby incorporated by reference herein in their entirety.

FIELD OF THE INVENTION

The present invention relates to a system for the improved imaging of eye structures, in particular in the eye anterior segment, based on optical coherence tomography.

BACKGROUND

Different methods and measuring devices are known for the tomographic imaging of eye structures, which are based on confocal scanning systems or optical coherence tomography (OCT).

Ophthalmoscopes based on confocal scanners, particularly confocal scanning laser ophthalmoscopes (cSLO), are an important tool for the diagnosis and therapy in ophthalmology (U.S. Pat. No. 6,769,769 B2). Confocal scanners can provide a three-dimensional spatial resolution by limiting the depth of a movable focus using spatial filtering and, contrary to OCT, do not rely on the use of interference effects.

By contrast, in OCT methods, coherent light for distance measurement and imaging is used on reflective and scattering samples using an interferometer. The OCT methods applied to the human eye provide measurable signals during a depth scan due to the changes of the refractive index occurring at the optical boundaries and due to volume scattering. Optical coherence tomography is a very sensitive and quick method for interferometric imaging which has become prevalent in the medical field and fundamental research (Wolfgang Drexler, James G. Fujimoto: "Optical Coherence Tomography Technology and Applications," Springer Publishing 2008). OCT images (OCT scans) of eye structures are frequently used in ophthalmology for diagnosis and therapy follow-up as well as planning of procedures and the selection of implants. The use of OCT scans of the retina for determining retinal nerve fiber layers (RNFL) for the diagnosis of glaucoma and monitoring of the progress of the disease is one example for the OCT-supported diagnosis.

For example, the basic principle of the OCT method described in U.S. Pat. No. 5,321,501 is based on white light interferometry and compares the travel time of a signal using an interferometer (most commonly a Michelson interferometer). The arm with known optical path length (=reference arm) is used as reference for the measurement arm, which holds the sample. The interference of the signals from both arms yields a pattern for determining the scattering amplitudes on the basis of the optical delays between the arms and thus a scattering profile, which, analogous to ultrasonics, is called A-scan. Quick variations of the optical delay between measurement arm and reference arm can, e.g., be realized using fiber lines (EP 1 337 803 A1) or so-called rapid-scanning optical delays (RSOD) (U.S. Pat. No. 6,654,127 B2). In the multidimensional scanning grid methods, the beam is guided transversely in one or two directions, allowing for the recording of a two-dimensional B-scan or a three-dimensional volume tomogram. When the length of the reference arm is held constant, a two-dimensional C-scan can be obtained with lateral scanning of the measuring beam in two directions.

An important example for the use of optical coherence tomography is the biometry in the eye anterior segment using an anterior chamber OCT (AC-OCT), allowing for the subsequent selection of implants, such as intraocular lens implants (IOL's), particularly also phakic IOL's for a refractive correction. However, IOL's are most commonly used for replacing the natural crystalline lens in case of a clouding of the lens (cataract), wherein refractive and imaging errors are also increasingly corrected.

In addition to OCT, optical coherence domain reflectometry is used for interferometric biometry, which allows for the determination of intraocular distances, which are required as biometric parameters for the selection of IOL's (US 2005/018137 A1, U.S. Pat. No. 7,400,410 B2).

The most important biometric parameters are axis length (distance between cornea and retina), corneal curvature and refractivity, and the depth of the anterior chamber (distance to the crystalline lens). In order to ensure the best possible vision after surgery, it is necessary to determine these biometric parameters with adequately high accuracy. The selection of a suitable replacement lens using the determined measurements is based on established formulas and calculation methods.

The basic principle of the OCT method is based on white light interferometry or short coherence interferometry and interferometrically compares the travel time of a backscattered sample signal (or measuring signal) with a reference signal using an interferometer (most commonly a Michelson interferometer). This allows not only for the analysis of reflections on surfaces but also of slight, varying scattering signals from different sample depths.

The arm with known optical path length (=reference arm) is used as reference for the measurement arm (also called sample arm). The interference of the signals from reference arm and sample arm generates an interference pattern for determining the relative optical path length of scattering signals within an A-scan (depth signal). In one-dimensional scanning grid methods, the beam is then, analogous to ultrasonics, guided transversely in one or two directions, allowing for the recording of a two-dimensional B-scan, a C-scan or a three-dimensional tomogram. Typically, a C-scan is a two-dimensional tomogram, which was obtained through two-dimensional scanning at constant reference arm length in a time-domain OCT. However, in the following, said term shall be used as synonym for all scans which are based on two-dimensional scanning, thus also for volume scans. Here, the amplitude values of the individual A-scans are depicted as linear or logarithmic grey-level or pseudo-color values. It is also known that volume scans can be corrected by comparing them with B-scans with regard to interferences caused by sample movements (U.S. Pat. No. 7,365,856). Furthermore, it is known that a phase-resolved measurement, particularly by Doppler signal analysis, can be used to generate and present additional information about dynamic processes (Adrian H. Bachmann, Martin L. Villiger, Cedric Bluffer, Theo Lasser, and Rainer A. Leitgeb: "Resonant Doppler flow imaging and optical vivisection of retinal blood vessels," Vol. 15, No. 2/OPTICS EXPRESS 408).

A-scans are commonly recorded with 400 Hz to 400 kHz, in exceptional cases even in the MHz range. Ophthalmologic OCT systems have typical sensitivities of 80 dB to 110 dB. The utilized wavelength depends on the desired scan region and the absorption and scattering behavior of the tissue. Retinal OCT's frequently operate in the range of 700 nm to 1100 nm, while anterior chamber OCT's preferably use longer wave radiation, e.g., 1300 nm, which is absorbed in the vitreous humor. Anterior chamber OCT's can also be realized through switchover from retinal OCT's (US 2007/0291277 A1).

The axial measurement resolution of the OCT method is determined by the so-called coherence length of the applied light source, which is inversely proportional to the bandwidth of the applied radiation and typically lies between 3 µm and 30 µm (short coherence interferometry). The lateral measurement resolution is determined by the profile of the measuring beam in the scan region and lies between 5 µm and 100 µm, preferably below 25 µm. Due to its particular suitability for the examination of optically transparent media, this method is widespread in ophthalmology.

Two different basic types of OCT procedures have prevailed among those used in the field of ophthalmology. With the first type, the reference arm is modified in length to determine the measured data and continually measure the intensity of the interference without taking the spectrum into account. This procedure is called "Time Domain" procedure (U.S. Pat. No. 5,321,501 A). With the other procedure, called "Frequency Domain" procedure, however, the spectrum is taken into account for determining the measurements and the interference of the individual spectral components is recorded. Therefore, one is a signal within the time domain, and the other is a signal within the frequency domain.

The advantage of the frequency domain is the simple and quick simultaneous measuring, wherein complete information about the depth can be determined without requiring movable parts. This increases both stability and speed (U.S. Pat. No. 7,330,270 B2).

In frequency domain OCT, a further differentiation is made by obtaining the spectral information either with the use of a spectrometer ("spectral domain OCT", or SD-OCT) or spectral tuning of the light source ("swept source OCT", or SS-OCT).

The big technological advantage of the OCT is the decoupling of the depth resolution from the transverse resolution. In contrast to microscopy, this allows for the recording of the three-dimensional structure of the object to be examined. The purely reflective and thus contact-free measuring makes it possible to generate microscopic images of live tissue (in vivo).

DE 196 24 167 A1 describes a method for coherence biometry and tomography with increased transverse resolution. The position of light emitting points along a measurement path on the surface and on the inside of objects is measured using a measuring light beam of a short coherence interferometer. Short coherence interferometry in this context basically means that light with a short coherence length is used and the length to be measured in the measuring beam is determined such that the length in the reference beam is continuously changed until interferences occur, which is only the case when the two beam paths within the coherence length of the applied light are at equal length. As a result, the known length of the reference beam equals the sought length in the measuring beam.

With the method for coherence biometry, the entire depth of the measuring object in z-direction is detected with a measuring beam, while a whole series of such interferometric distance measurements (e.g., in x-direction) are carried out at adjacent points and assembled to an image with coherence tomography.

The light beam illuminating the object is shifted relative to the object, e.g., in x-direction after every A-scan, and so the object structure is scanned line by line in z-direction. These lines are subsequently assembled to a cross-sectional image (tomogram).

With the described solution, an equally good and high transverse resolution along the entire interferometric measurement path is achieved such that a suitable optical imaging of the (dynamic) focus in the object generated by the moved optical element ensures the simultaneous alignment of the optical lengths of reference beam path and measurement beam path right up to the (thus coherent) measuring focus.

Additional polarization-effective, optical components can be used for reducing reflection losses on the surfaces of the components and for optimizing the beam splitter of the described interferometer system.

An efficient optical coherence tomography system for quick, three-dimensional imaging is described in U.S. Pat. No. 7,145,661 B2. Light which is polarized using a polarization beam splitter is impinged into the OCT system, and so the OCT detector operates in a low-noise system.

When an eye is scanned, the system detector can simultaneously generate a pixel image with a low frequency component and a pixel image with a high frequency component of every point. While the pixel image with a low frequency component resembles that of an image realized with a scanning laser ophthalmoscope (SLO), the image with a high frequency component corresponds to that of a two-dimensional OCT image. Due to the pixel-to-pixel correspondence between the simultaneously recorded SLO and OCT images, the OCT image can be converted for the entire region pixel by pixel "on the fly" into a 3D image in accordance with the SLO image.

The described solution provides a system for realizing precise three-dimensional OCT images of the eye tissue in an extremely fast manner.

The not yet published document DE 10 2009 041 996.9 relates to an ophthalmological biometry or imaging system and a method for detecting and evaluating measured data, determining variables, distances and/or geometric relationships of eye structures. For optimizing the detection of the measured values, the measurement arrangement has, among others, a control circuit, which is formed by a control unit, an optical scan unit and a position sensor. In a disclosed embodiment, polarization is adjusted between measurement arm and reference arm of the OCT interferometer in order to ensure sufficient signal strengths preferably in all regions of the scan. The polarization adjustment can be made, for example, through rotated birefringent wave plates, motor-driven fiber paddles, birefringent or polarization-rotating liquid crystal modulators, or fast electro-optical polarization modulators.

US 2007/291277 A1 describes a further optical coherence tomography system, which is preferably based on a Mach-Zehnder interferometer. Once again, polarization is adjusted between measurement arm and reference arm of the interferometer in order to ensure sufficient signal strengths in all regions of the scan, wherein fiber paddles are used for said purpose. However, it is frequently not possible to detect all central and peripheral cornea regions evenly well with the adjustment of said fiber paddles. There is also the particular problem that depth-dependent changes in the polarization state of the backscattered light can also be observed in the cornea.

As is known, the strength of OCT signals depends on the adjustment of the polarization states of the superimposed light from sample arm and reference arm of the OCT interferometer. At equal polarization states, maximal interferences are achieved but with polarization states that are orthogonally oriented to one another (e.g., linearly or circularly), no interference signals can be detected.

Deviations between the polarization states can be caused, e.g., by different beam guidances in sample arm and reference arm, e.g., by mirrors in a periscope arrangement or polarization-effective, optical components. Birefringent samples, such as corneas, crystalline lenses, or retinal nerve fiber layers of the human eye can also cause said deviations.

According to the solutions from the known prior air, the polarization in OCT systems is in part or predominantly adjusted with adjustable optical elements which influence the polarization effect, wherein fiber paddles are used most frequently which are fiber loops that can be rotated manually or with a motor. With birefringence, fiber paddles have a similar effect as known wave plates.

However, despite the use of optical elements for polarization adjustment, the solutions known from the prior art are not capable of obtaining optimized signals from samples with depth-dependent, polarization-changing effect.

Another example is the measurements at the birefringent, retinal nerve fiber layer (RNFL), the thickness evaluation of which is very important for diagnosing glaucoma and glaucoma progression analysis. Elaborate polarization-resolved measurements using scanning laser ophthalmoscopes (SLO) are known. OCT signals can be recorded polarization-resolved using so-called polarization-sensitive OCT systems (PS-OCT), wherein separate detection paths are realized for orthogonally polarized light portions. Yasuno et al. (Optics Express Vol. 17, Iss. 5, pp. 3980-3996 (2009)) describes a PS-OCT system for the anterior chamber region which is based on the swept-source frequency-domain optical coherence tomography.

For example, the resulting interference spectra of two orthogonally polarized reference light portions which are each superimposed with the backscattered sample light are recorded separately in an SD-OCT system using two spectrometers.

Separate detection channels can also be realized by temporally fast multiplexing, using very fast polarization modulators, such as acousto-optical modulators (AOM), electro-optical modulators (EOM) or Piezo fiber stretcher.

It is disadvantageous that all these systems are very elaborate with regard to their beam guidance, polarization separation, separated detection or realization of high-frequency and high-precision modulation signals and do not achieve an optimal signal-to-noise ratio under certain circumstances.

Example

Sample light has by accident already been optimally polarization-adjusted with regard to a detection channel. Due to the necessary separation of the sample light onto two detection channels (e.g., 50:50), one channel can only detect one signal, which contains 50% of the sample light (SNR reduced by 3 dB relative to optimum) while nothing is detected in the other channel.

When OCT methods are used for imaging the eye anterior segments, it has to be taken into account that the image quality and the visibility of the cornea and other intraocular structures and implants are dependent on and, under certain conditions, limited by the illumination conditions and illumination settings, such as contrast, brightness, noise performance, saturation, and polarization. Even though these settings can be optimized by the user, imaging of some of the structures, particularly intraocular lenses (IOL), is very difficult.

Carl Zeiss Meditec AG developed Stratus OCT™, a device for high-resolution optical coherence tomography as a non-contact procedure for examining the eye anterior segments, particularly for the diagnosis and follow-up of retinal diseases. With the introduction of the Visante™ OCT system, high-resolution, non-contact, optical coherence tomography can also be used for the eye anterior segments. The Visante™ OCT system provides clear and detailed cross-sectional images of the anterior chamber, including the chamber angle, without requiring typical anesthesia or a time-consuming water bath. The image quality is improved by an extended scan mode, wherein four consecutive scans are carried out with the same settings and the measured values are averaged in the result. The averaged image, when compared to single scan images, has a higher resolution and improved noise performance. However, the imaging of certain structures, particularly implants, remains difficult despite these significant improvements. Furthermore, this OCT system also allows for recording radial meridian scans of the anterior chamber, e.g., for determining the thickness distribution of the cornea.

The signal processing in OCT is based on the assumption that the polarization state of the reference light corresponds to the polarization state of the sample light. However, practice has shown that structures and/or implants can indeed change the polarization state of the sample light. In extreme cases, the polarization states of sample light and reference light can be perpendicular to each other, and so no interference pattern can occur because the OCT signal disappears completely.

With the use of a polarization controller, the polarization state of the light source can be changed such that the previously described effect is minimized. However, optimizing the settings is very time-consuming, even with the presence of a polarization controller in the OCT system. Furthermore, only one polarization state is determined for a longer interval of seconds to minutes. Imaging of structures with differently changed polarization always requires changes of the polarization state. Therefore, different structures are not optimally visible at the same time.

SUMMARY OF THE INVENTION

The problem addressed by the present invention is that of developing a solution for improved imaging of eye structures, particularly in the eye anterior segment, which allows for the realization of clear and detailed cross-sectional images of the anterior chamber, including the chamber angle. In particular, the solution is also suitable for efficiently obtaining optimized OCT signals from samples with location-dependent and/or depth-dependent, polarization-changing effect. The solution provides support for surgical planning and postoperative follow-up and preferably involve a non-contact method.

According to the invention, the problem is solved by the features disclosed herein.

This problem is solved with the present system for the improved imaging of eye structures, in particular in the eye anterior segment, comprising an interferometric measuring arrangement with a measurement arm and a reference arm, a light source for illuminating the measurement arm and the reference arm, an optical element arranged in the measurement arm or reference arm for influencing the polarization state of the light in the measurement arm or reference arm before the light is interferometrically superimposed, a scanning unit arranged in the measurement arm for implementing OCT scans, a detector for recording the produced interference patterns, and an evaluating and documenting unit, wherein the optical element arranged in the measurement arm or reference arm of the interferometric measuring arrangement is designed to produce at least two different polarization states of the light in the measurement arm or reference arm, the detector is designed for recording the interference pattern produced in the interferometric measuring arrangement when illuminated with light having at least two different polarization states, an existing control module has connections to the scanning unit, the optical element for influencing the polarization state of the light in the measurement arm or reference arm, the detector, and the evaluating and documenting unit, and the evaluating and documenting unit is designed to reconstruct and combine OCT scans from the interference patterns transmitted by the detector and present and/or store the resulting OCT signals.

According to the invention, the system for the improved imaging of eye anterior segments, which is based on optical coherence tomography, can be used for pre- and postoperative imaging for analysis and measurement. In addition to the exact measurement of the eye structures in the anterior segment, including anterior chamber depth, anterior chamber angle, and anterior chamber diameter, the solution is also suitable for imaging, measuring, and documenting the flap thickness and residual stroma thickness immediately following the LASIK treatment.

In addition to the above applications, the solution for the improved imaging of eye anterior segments can also be used for pachymetry because it generates high-resolution cornea scans with quick imaging, and a precise and reproducible corneal thickness map can be determined from said scans for the use in refractive surgery and glaucoma diagnostics.

BRIEF DESCRIPTION OF THE DRAWINGS

In the following, the invention is further described in terms of embodiments.

DETAILED DESCRIPTION

The system for the improved imaging of eye structures, in particular in the eye anterior segment, according to the invention, comprises an interferometric measuring arrangement with a measurement arm and a reference arm, a light source for illuminating the measurement arm and the reference arm, an optical element arranged in the measurement arm or reference arm for influencing the polarization state of the light in the measurement arm or reference arm before the light is interferometrically superimposed, a scanning unit arranged in the measurement arm for implementing OCT scans, a detector for recording the produced interference patterns, and an evaluating and documenting unit. The optical element arranged in the measurement arm or reference arm of the interferometric measuring arrangement is designed to produce at least two different polarization states of the light in the measurement arm or reference arm. The detector is designed for recording the interference pattern produced in the interferometric measuring arrangement when illuminated with light having at least two different polarization states. An existing control module has connections to the scanning unit, the optical element for influencing the polarization state of the light in the measurement arm or reference arm, the detector, and the evaluating and documenting unit. The evaluating and documenting unit is designed to reconstruct and combine OCT scans from the interference patterns transmitted by the detector and present and/or store the resulting OCT signals.

It is advantageous when the light source provides light of a sufficiently stable, defined polarization state, i.e., when the light has a degree of polarization (DOP-degree of polarization) for example between 1:3 and 1:1000, as another example, between 1:10 and 1:200, and creates signal fluctuations, which are dependent on the polarization state, of less than 25%, and which are measured by an analyzer that is aligned with respect to maximal transmission. This ensures a sufficient signal-to-noise ratio and a sufficient effect of the optical elements for influencing the polarization state.

The interference of the signals (optical cross-correlation) from measurement arm and reference arm of the interferometric measuring arrangement results in an interference pattern from which the relative optical path length within a depth profile (A-scan) can be obtained. In the one-dimensional scanning grid methods, the light beam from the scanning unit is guided transversely in one or two directions, allowing for the recording of a two-dimensional tomogram (B-scan) or a three-dimensional volume (C-scan).

The prominent property of the OCT method is the decoupling of the transverse resolution from the longitudinal resolution. In conventional light microscopy, the axial resolution (in the depth) and the transverse (lateral) resolution depends on the focusing of the light beam. The parameter for the focusability is the numerical aperture. In OCT, the axial resolution is only limited by the bandwidth of the applied light; therefore, a higher resolution and thus smaller details can be resolved with a large bandwidth (with broad spectra). The use of short coherent light can ensure a high axial spatial resolution.

The polarization state of the illumination light can be influenced either in the measurement arm or the reference arm of the interferometric measuring arrangement. This ensures that the polarization adjustment of the light is varied between the reference arm and the measurement arm before they are interferometrically superimposed.

While the use of at least one optical element prevents orthogonal polarization states, the use of a set of 3 or more optical elements allows for a complete adjustment of the polarization state. Preferably, at least one polarization optical element is used which can transform a linear state into a circular state, e.g., a quarter-wave plate.

λ-plates (wave plates), polarization rotators, in-line fiber polarization controllers, or fiber paddles are used as optical elements for influencing the polarization state of the illumination light. In principle, polarization-changing modulators, such as electro-optical, acousto-optical, or magneto-optical modulators are also suitable but the expenditure is significantly higher.

The inventors have discovered that fiber paddles have proven to be particularly advantageous because orthogonal states can be avoided. The polarization-changing effect is determined via the bending radius and bending angle of the birefringent fiber. For the realization of different polarization states, the fiber paddles have a positioning mechanism, which is connected to the control module in order to change the polarization states of the illumination light in predetermined or adapted steps on the basis of the signal ratios.

In order to obtain improved images of the eye anterior segments using the interferometric measuring arrangement, it is necessary for the optical element to realize at least two, but preferably three, defined polarization states of the illumination light for the measurements.

The evaluating and documenting unit combines the reconstructed OCT scans pointwise or zoned or completely in the form of A-, B-, or also C-scans. In this context, it has become apparent that it is expedient to evaluate the reconstructed OCT scans with regard to the relative shifts or deformations to one another and to correct said scans, if necessary (registration). Furthermore, the evaluating and documenting unit is also designed to combine the reconstructed OCT scans by generating weighted or unweighted mean, maximum, or even median values. The required weighting factors are generated from the local contrast, the attainment of minimum and maximum values, or the exceeding of threshold values for signal intensities, or the signal-to-noise ratio.

The control module with its functions can also be integrated in the evaluating and documenting unit.

Figure 1:
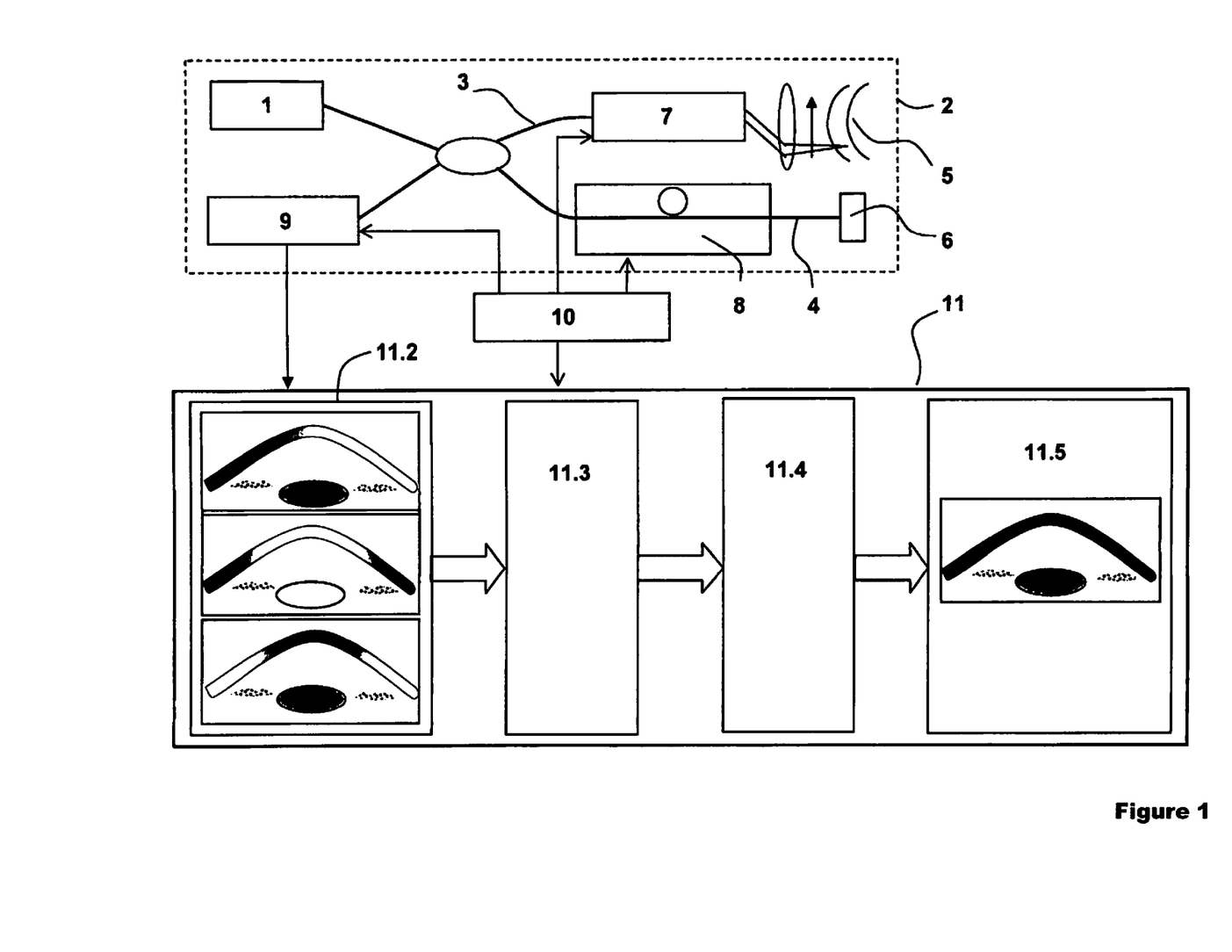
FIG. 1 depicts a system for recording three scans at predetermined polarization states.

In a first example embodiment, three OCT scans are recorded at predetermined, defined polarization states using the system according to FIG. 1.

Proceeding from the light source 1, the object 5 located in the measurement arm 3 of an interferometric measuring arrangement 2, and the mirror element 6 arranged in the reference arm 4 of the object 5 and movable between measurement arm and reference arm for path length compensation in the direction of the light beam are illuminated with short coherent light. In addition, the interferometric measuring arrangement 2 has a scanning unit 7 in its measurement arm 3 for realizing OCT scans in the form of A-, B-, and C-scans, and an optical element arranged in its reference arm 4 for influencing the polarization state of the illumination light in the form of a fiber paddle 8 with positioning mechanism. A detector 9 for recording the short coherent light reflected from the object 5 and the mirror element 6 is positioned at the end of the interferometric measuring arrangement 2. The existing control module 10 is connected to and controls the scanning unit 7, the positioning mechanism of the fiber paddle 8 and the detector 9. The detector 9 forwards the recorded interference pattern to an evaluating and documenting unit 11, which reconstructs and combines said interference patterns to OCT scans and presents and stores the resulting OCT signals.

For the recording of three interference patterns, the existing control module 10 transmits to the positioning mechanism of the fiber paddle 8 the positions for the realization of the three different, predefined polarization states of the illumination light. After these three interference patterns are reconstructed 11.2 to OCT scans by the evaluating and documenting unit 11, said patterns are combined 11.4 to OCT signals and presented and/or stored 11.5 by the evaluating and documenting unit 11. For the purpose of clarifying the differences of the interference patterns recorded at different polarization states, their resulting reconstruction 11.2 to OCT scans and their presentation and/or storage 11.5 is depicted schematically.

Said combining 11.4 can be generated by weighted and unweighted mean, maximum, or even median values. It is expedient that the evaluating and documenting unit 11 registers 11.3 the three interference patterns prior to combining 11.4 them to resulting OCT signals. During registration, the interference patterns are evaluated with regard to shifts relative to one another and corrected, if necessary.

The registration of OCT scans which, depending on the polarization, can exhibit partial or complete signal failures, presents a particular challenge. According to the invention, this problem is solved by using a very strong signal portion (e.g., the surface of iris or cornea), which provides signals sufficient for the registration even at unfavorable polarization states. It is also possible to use methods for signal registration that are known to a person skilled in the art, wherein incomplete signal portions are completed in accordance with specific plausibility criteria and weightings. For example, weighted fits or curve fittings of the anterior or posterior surface of the cornea or its focal point are suitable methods. Suitable weighting parameters, e.g., are the strength and sharpness of an intensity jump of the signal-to-noise ratio, which is a measure for the probability of the presence of a cornea surface at this position.

Figure 2:
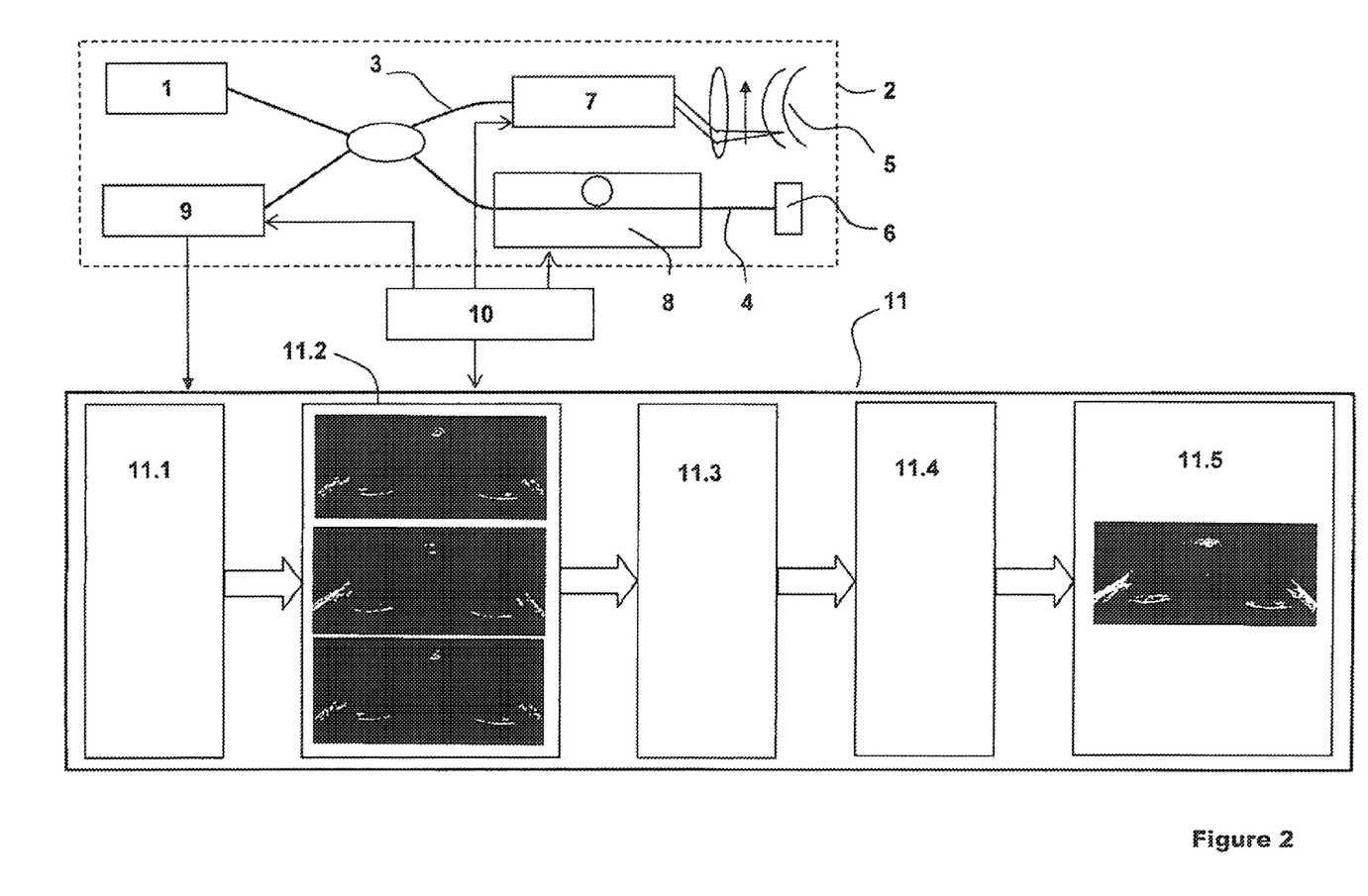
FIG. 2 depicts a system for the adaptive determination of suitable polarization states.

In a second example embodiment, three scans at adaptively determined polarization states are recorded using the system according to FIG. 2.

The overall system corresponds to that of the first example embodiment according to FIG. 1, except that the evaluating and documenting unit 11 has an additional signal evaluation 11.1. This signal evaluation 11.1 evaluates the interference pattern, which was recorded and transmitted by the detector at a first polarization state, prior to its reconstruction 11.2 to OCT scans with regard to specific criteria in order to determine adapted polarization states.

Contrary to FIG. 1, the OCT scans as the result of their reconstruction 11.2 and their presentation and/or storage 11.5 are not depicted schematically, but as real images of an eye.

Applicable criteria, e.g., are contrast, the attainment of minimum and maximum values, or the exceeding of threshold values for signal intensities, or the signal-to-noise ratio.

The signals can also be evaluated without a complete reconstruction of the OCT scans. For example, the contrast of spectral interference modulations can be evaluated without an elaborate complete signal reconstruction using Fourier transforms.

Once a series of at least two, but preferably three, adapted polarization states of the illumination light have been determined, the three interference patterns are recorded. For this purpose, the existing control module 10 transmits the positions for realizing the three adapted polarization states to the positioning mechanism of the fiber paddle 8.

In this second example embodiment, the three interference patterns are recorded by the detector 9 and transmitted to the evaluating and documenting unit 11 which, after reconstructing 11.2 said three interference patterns to OCT scans, combines 11.4 said scans and presents and/or stores 11.5 the resulting OCT signals. Once again, the combining 11.4 can be generated by weighted and unweighted mean, maximum, or also median values. It is expedient that the evaluating and documenting unit 11 registers 11.3 the three interference patterns prior to combining 11.4 them to resulting OCT signals, wherein the interference patterns are evaluated and corrected, if necessary, with regard to shifts relative to one another.

Figure 3:
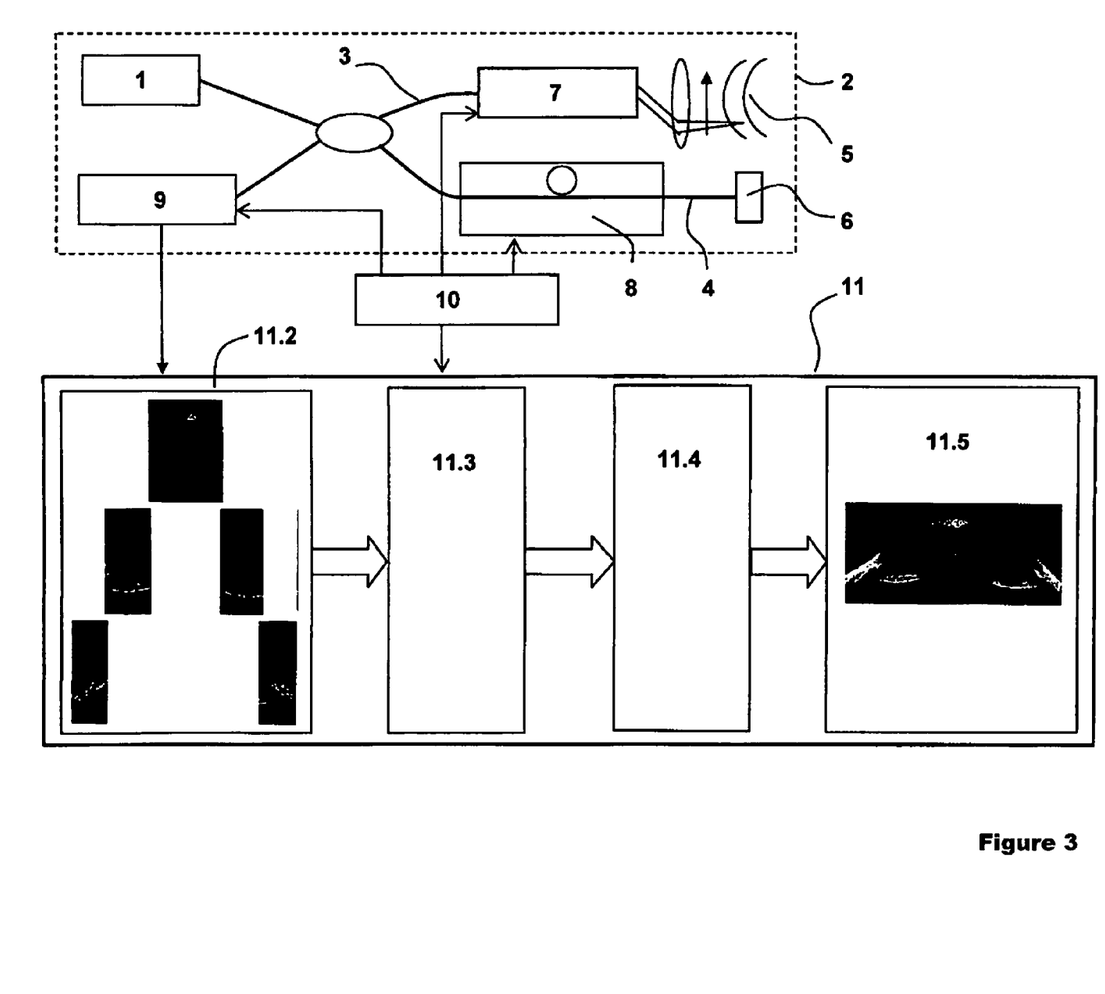
FIG. 3 depicts a system for recording zoned scans at different polarization states.

In a third example embodiment, three zoned scans are recorded at different polarization states using the system according to FIG. 3.

Since the polarization states can be predetermined or adapted, the overall system can correspond to the first example embodiment according to FIG. 1 or the second example embodiment according to FIG. 2. The difference is merely that the detector 9 records and then transmits different zones instead of complete interference patterns to the evaluating and documenting unit 11.

Once again, the three interference patterns are reconstructed 11.2 to OCT scans by the evaluating and documenting unit 11. The OCT scans as the result of their reconstruction 11.2 and their presentation and/or storage 11.5 are, once again, not depicted schematically but as real images of an eye.

Contrary to the previously described solutions, the OCT scans are not combined 11.4 to resulting OCT signals using weighted and unweighted mean, maximum, or also median values but are assembled (added) from the partial or zone scans. This is followed by their presentation and/or storage 11.5.

It is particularly expedient that the evaluating and documenting unit 11 registers 11.3 the three zone-interference patterns prior to combining 11.4 them to resulting OCT signals, wherein the interference patterns are evaluated with regard to shifts relative to one another and corrected, if necessary. This is advantageous because the zones fit together perfectly without any blemishes. In this context, it is advantageous for the individual zones to be superimposed at least minimally, wherein favorable superimposition widths are between 100 μm and 1 cm. This allows for the compensation of depth-dependent polarization effects and facilitation of the registration.

The most essential advantage of this solution when compared to the previously described embodiments is the time saving aspect. For every zone to be scanned, an optimal polarization state can be determined and used. Therefore, a combination of generated weighted and unweighted mean, maximum, or also median values can be foregone.

For this third example embodiment, the scans to be combined do not necessarily have to be zone scans. Instead, it is also possible to combine complete scans with zone scans in order to save measuring time. For example, it is possible with zone scans to repeatedly scan and combine only the problematic, peripheral cornea regions at different polarization-adjustment states.

In the described systems for improved imaging of the eye anterior segments according to the invention, the polarization adjustment is varied between the measurement light and the reference light before they are interferometrically superimposed. After a spatial registration of the OCT scans for the evaluation, and, if necessary, correction of shifts relative to one another, the at least two, but preferably three, scans are combined for obtaining an optimal signal.

The use of 3 or more scans, in particular, also allows for the recording of intermediate states when parts of the OCT scans appear to be completely complementary for two polarization positions because a depth-dependent sample scattering in some places, e.g., causes polarization states which are orthogonal to one another. The signal coupling which can be realized with these intermediate states simplifies, e.g., a registration and dynamic processes can be evaluated using OCT which are based on the comparison of local states at different times, such as the evaluation of phase or speckle changes. Such evaluations can be used, e.g., for determining blood flows in vessels but also other movements.

In addition to the variation of the pure polarization adjustments, it is furthermore possible to change the spatial positions between the scans. For example, these scans can form the previously mentioned meridian scans. As a result, the improvement of the OCT signals according to the invention can be realized both through a combination of adjacent meridians and the known evaluation with regard to the thickness distributions of the cornea.

The proposed invention provides a solution for improved imaging of the eye anterior segments, which allows for the realization of clear and detailed cross-sectional images of the anterior chamber, including the chamber angle. In particular, the solution is suitable for efficiently obtaining optimized OCT signals from samples with location-dependent and/or depth-dependent, polarization-changing effect. The solution provides support for surgical planning and postoperative follow-up for applications on the eye anterior segment and is a non-contact method.

The proposed solution relates to the field of high-resolution, non-contact, optical coherence tomography for imaging eye structures, particularly in the eye anterior segment but can also be used for supporting surgical planning, diagnosis, and the follow-up of retinal diseases. It produces extremely clear and detailed cross-sectional images of the anterior chamber, including the chamber angle.

The invention claimed is:

1. A system for improved imaging of eye structures, including the eye anterior segment, comprising:
    an interferometric measuring arrangement having a measurement arm, a reference arm and a light source that illuminates the measurement arm and the reference arm;
    an optical element arranged in the measurement arm or the reference arm that influences a polarization state of light in the measurement arm or the reference arm before the light is interferometrically superimposed;
    a scanning unit arranged in the measurement arm that implements OCT scans;
    a detector that records produced interference patterns; and
    an evaluating and documenting unit;
    wherein the optical element arranged in the measurement arm or the reference arm of the interferometric measuring arrangement produces at least two different polarization states of the light in the measurement arm or the reference arm;
    wherein the detector records the produced interference pattern in the interferometric measuring arrangement when illuminated with light having at least two different polarization states;
    wherein a control module has operable connections to the scanning unit, the optical element for influencing the polarization state of the light in the measurement arm or the reference arm, the detector, and the evaluating and documenting unit; and
    wherein the evaluating and documenting unit reconstructs and combines to at least some extent, spatially superimposing OCT scans from the interference patterns transmitted by the detector and presents and/or stores reconstructed OCT scans.

2. The system according to claim 1, further wherein the optical element realizes at least two different polarization states of the light in the measurement arm or reference arm.

3. The system according to claim 2, further wherein the optical element realizes at least three different polarization states of the light in the measurement arm or reference arm.

4. The system according to claim 1, wherein the optical elements for influencing the polarization state of the illumination light in the measurement arm or reference arm comprise at least one structure selected from the following group: wave plates, polarization rotators, in-line fiber polarization controllers, and fiber paddles.

5. The system according to claim 1, wherein the optical elements for influencing the polarization state of the illumination light in the measurement arm or reference arm comprise structures selected from the following group a set of wave plates, a set of polarization rotators, a set of in-line fiber polarization controllers, and a set of fiber paddles.

6. The system according to claim 1, wherein the optical element for realizing different polarization states of the illumination light in the measurement arm or reference arm further comprises a positioning mechanism which is connected to the control module to change the polarization states of the illumination light in predetermined or adapted steps.

7. The system according to claim 1, wherein the evaluating and documenting unit evaluates the interference pattern detected and transmitted by the detector at a first polarization state of the light in the measurement arm or reference arm with regard to specific criteria selected from a group consisting of: contrast, the attainment of minimum and maximum values, the exceeding of threshold values for signal intensities, or a signal-to-noise ratio.

8. The system according to claim 1, wherein the evaluating and documenting unit combines the reconstructed OCT scans pointwise or zoned or completely in the form of A-scans, B-scans, or C-scans.

9. The system according to claim 1, wherein the evaluating and documenting unit evaluates and, if necessary, corrects the reconstructed OCT scans with regard to shifts of one reconstructed OCT scan relative to one another of the reconstructed OCT scans.

10. The system according to claim 1, wherein the evaluating and documenting unit combines the reconstructed OCT scans by generating weighted or unweighted mean, maximum, or median values.

11. The system according to claim 1, wherein the evaluating and documenting unit generates weighting factors from local contrast, the attainment of minimum and maximum values, the exceeding of threshold values for signal intensities, or a signal-to-noise ratio.

12. The system according to claim 1, wherein the control module with its functions is integrated in the evaluating and documenting unit.

13. The system according to claim 1, wherein the light source has a stable degree of polarization between 1:3 and 1:1000.

14. The system according to claim 13, wherein the light source has a stable degree of polarization between 1:10 and 1:200.

15. The system according to claim 1, wherein the evaluating and documenting unit evaluates the OCT scans realized and recorded in at least 3 different polarization states with regard to dynamic changes, particularly using Doppler signal analysis.

16. The system according to claim 15, wherein the evaluating and documenting unit evaluates the OCT scans realized and recorded in at least 3 different polarization states with regard to dynamic changes using Doppler signal analysis.

* * * * *

UNITED STATES PATENT AND TRADEMARK OFFICE
CERTIFICATE OF CORRECTION

| | | |
|---|---|---|
| PATENT NO. | : 8,801,184 B2 | Page 1 of 1 |
| APPLICATION NO. | : 13/696030 | |
| DATED | : August 12, 2014 | |
| INVENTOR(S) | : Martin Hacker et al. | |

It is certified that error appears in the above-identified patent and that said Letters Patent is hereby corrected as shown below:

In the Specification
Col. 2, line 58, delete "Bluffer" and insert -- Blatter --

Signed and Sealed this
Third Day of March, 2015

Michelle K. Lee
*Deputy Director of the United States Patent and Trademark Office*